US00PP12480P2

(12) United States Plant Patent
Fitch

(10) Patent No.: US PP12,480 P2
(45) Date of Patent: Mar. 19, 2002

(54) PAPAYA PLANT NAMED 'POAMOHO GOLD'

(75) Inventor: Maureen M. M. Fitch, Aiea, HI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/490,039

(22) Filed: Jan. 24, 2000

(51) Int. Cl.[7] ..... A01H 5/00
(52) U.S. Cl. ..... Plt./156
(58) Field of Search ..... Plt./156

(56) References Cited

PUBLICATIONS

U.S. patent application Ser. No. 09/300,960, 'UH Rainbow'.
U.S. patent application Ser. No. 09/301,398, 'UH Sun Up'.

*Primary Examiner*—Bruce R. Campell
*Assistant Examiner*—Kent L. Bell
(74) *Attorney, Agent, or Firm*—Margaret A. Connor; M. Howard Silverstein; John D. Fado

(57) ABSTRACT

A new and distinct variety of papaya (*Carica papaya L.*) plant cv. 'Poamoho Gold' which is characterized by having the following combination of characteristics that are desirable in a new variety: medium fruit size, distinctive spicy flavor, high degree of sweetness, absence of strong odor, attractive deep orange-yellow flesh color, attractive bulbous pyriform-shaped fruit with smooth, shiny, waxy skin generally free of grooves and roughness, resistance to papaya ringspot virus, high tree vigor, intermediate fruit bearing height, low incidence of carpellody and sterility, and moderately firm flesh, giving good eating, handling, and shipping qualities.

3 Drawing Sheets

BACKGROUND OF THE INVENTION

1. Field of the Invention

The present invention relates to a new and distinct variety of papaya (*Carica papaya L.*) plant, which will hereinafter be denominated varietally as 'Poamoho Gold'. More particularly, the invention relates to the asexual propagation of *Carica papaya L.* cv. 'Poamoho Gold'. The new variety is a fresh market papaya for use in local markets as well as for long distance shipping.

2. Description of the Art

'Poamoho Gold' is a backcross 1 (second generation) hybrid produced by crossing Hawaii's major export variety, 'Kapoho' (pollen parent, unpatented) with an unnamed plant from the F2 progeny (seed parent) of a genetically engineered hybrid papaya 'UH Rainbow' (U.S. Plant patent application Ser. No. 09/300,960) which has resistance to papaya ringspot virus (PRSV), an aphid-transmitted virus which is a major disease pathogen affecting papaya production worldwide. 'UH Rainbow' is an F1 hybrid produced by crossing Hawaii's standard export variety 'Kapoho' (unpatented) with a genetically engineered, PRSV-resistant papaya, 'UH SunUp' (U.S. Plant patent application Ser. No. 09/301,389), a red-fleshed papaya derived from the cultivar 'Sunset'. The pollen parent 'Kapoho' grown in Kahaluu, Hi., is a selection from a line discovered in the Kapoho region of Hawaii many years ago. The name of the line from which 'Kapoho' was derived is unknown.

The first backcross generation (BC1) seedlings from an unnamed plant of 'UH Rainbow' F2×'Kapoho' crosses were grown in Poamoho, Kunia, Helemano, Keaau, and Kapoho, Hi. Trees at the Poamoho site were measured monthly for trunk diameter, tree height, and date and height of first flowers. At fruiting, 9 months after transplanting to the field, fruits were harvested monthly for 10 months to record sugar content, firmness, weight, shape, flavor, and flesh color.

One of the backcross generation (BC1) seedlings was selected and named 'Poamoho Gold'. This new hybrid variety of papaya plant has been asexually reproduced by both micropropagation and rooted cuttings at the U.S. Department of Agriculture-Agricultural Research Service/Hawaii Agriculture Research Center research laboratory and greenhouse in Aiea and Maunawili, Hi., respectively. Trees reproduced by both of these methods have shown that the characteristics of this new papaya are stable and reproduce true to type in successive generations.

SUMMARY OF THE INVENTION

The new variety cv. 'Poamoho Gold' may be distinguished from other commercial papaya cultivars known to me by a combination of characteristics, including medium fruit size, distinctive spicy flavor, high degree of sweetness, absence of a strong odor that is unpleasant to some consumers, pleasing deep orange-yellow flesh color, smooth, waxy, and shiny skin quality generally free of deep grooves and lumps, attractive bulbous pyriform-shaped fruit, PRSV-resistance, high tree vigor, intermediate fruit bearing height, low incidence of sterility and carpellody (a low temperature response wherein the stamens and carpels fuse and form a disfigured, unmarketable fruit), and moderately firm flesh, giving good eating, handling, and shipping qualities.

BRIEF DESCRIPTION OF THE DRAWINGS

The accompanying drawings are color photographs showing plants with trunks, leaves, and fruit of the new variety.

DETAILED BOTANICAL DESCRIPTION

Figure 1:
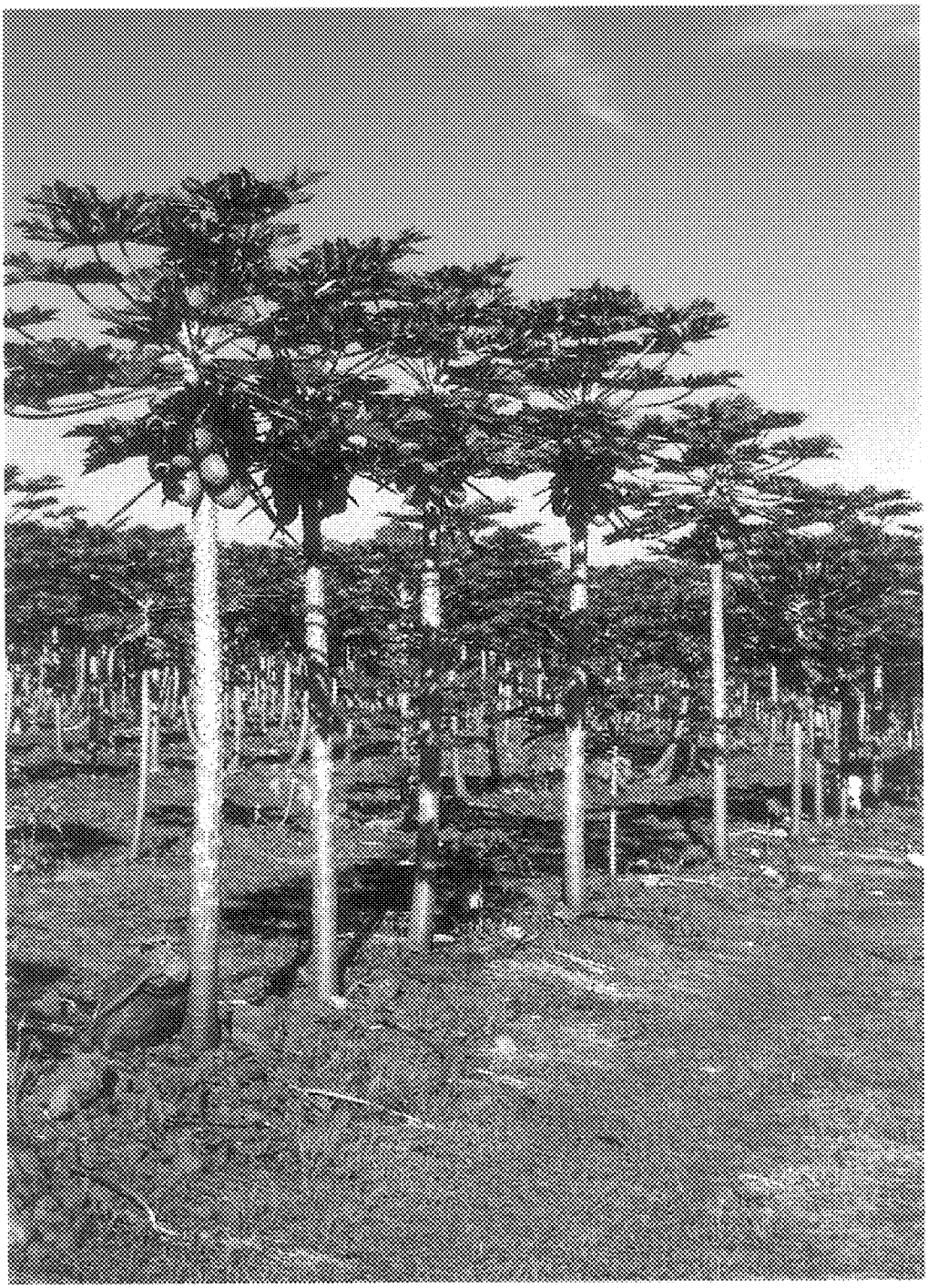
FIG. 1 shows the new variety in a field planting and is as representative as possible of the vegetative characteristics and of the full fruit column.
Figure 2:
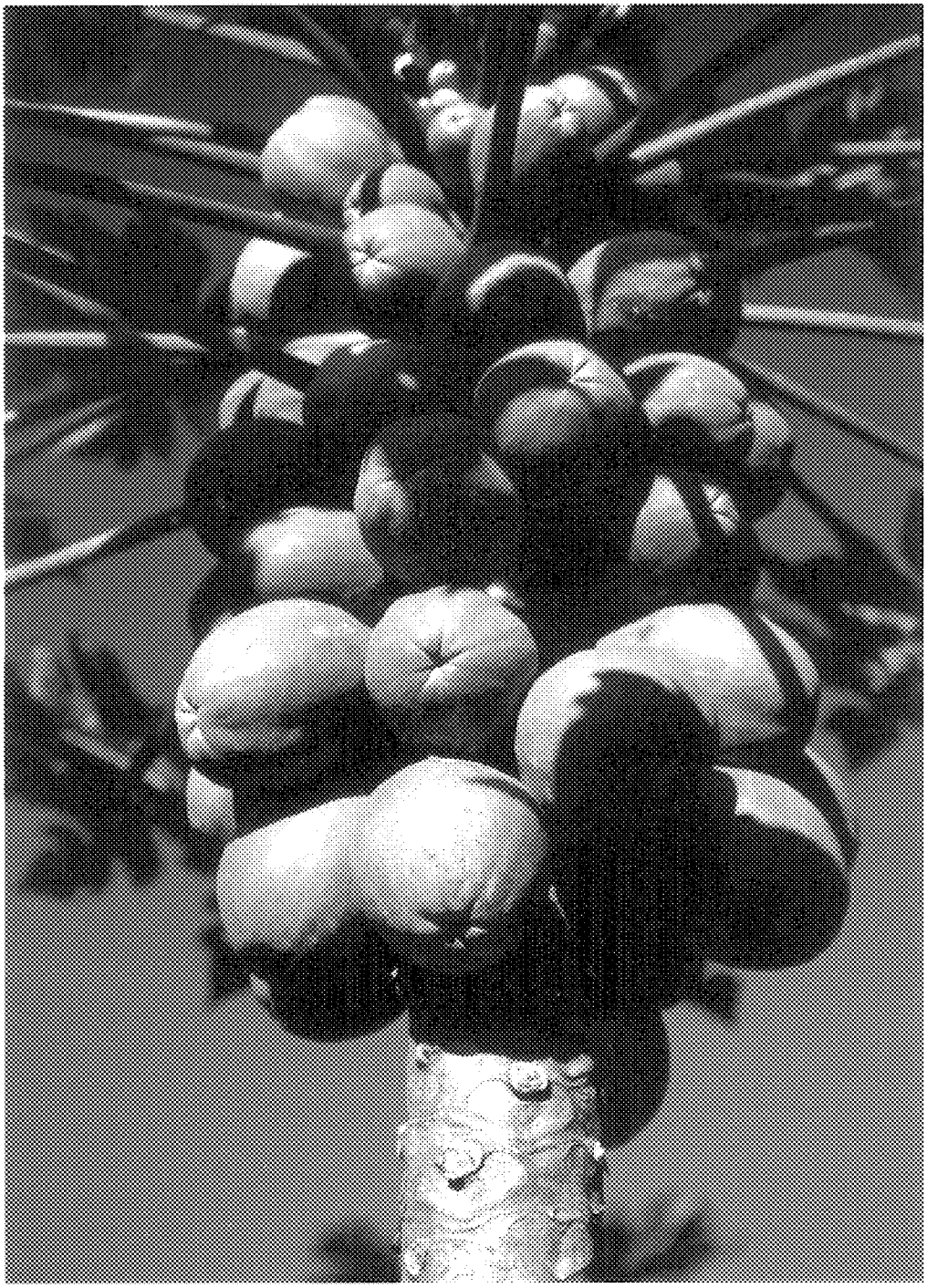
FIG. 2 is a closer view of the characteristic mature fruits just prior to harvest.
Figure 3:
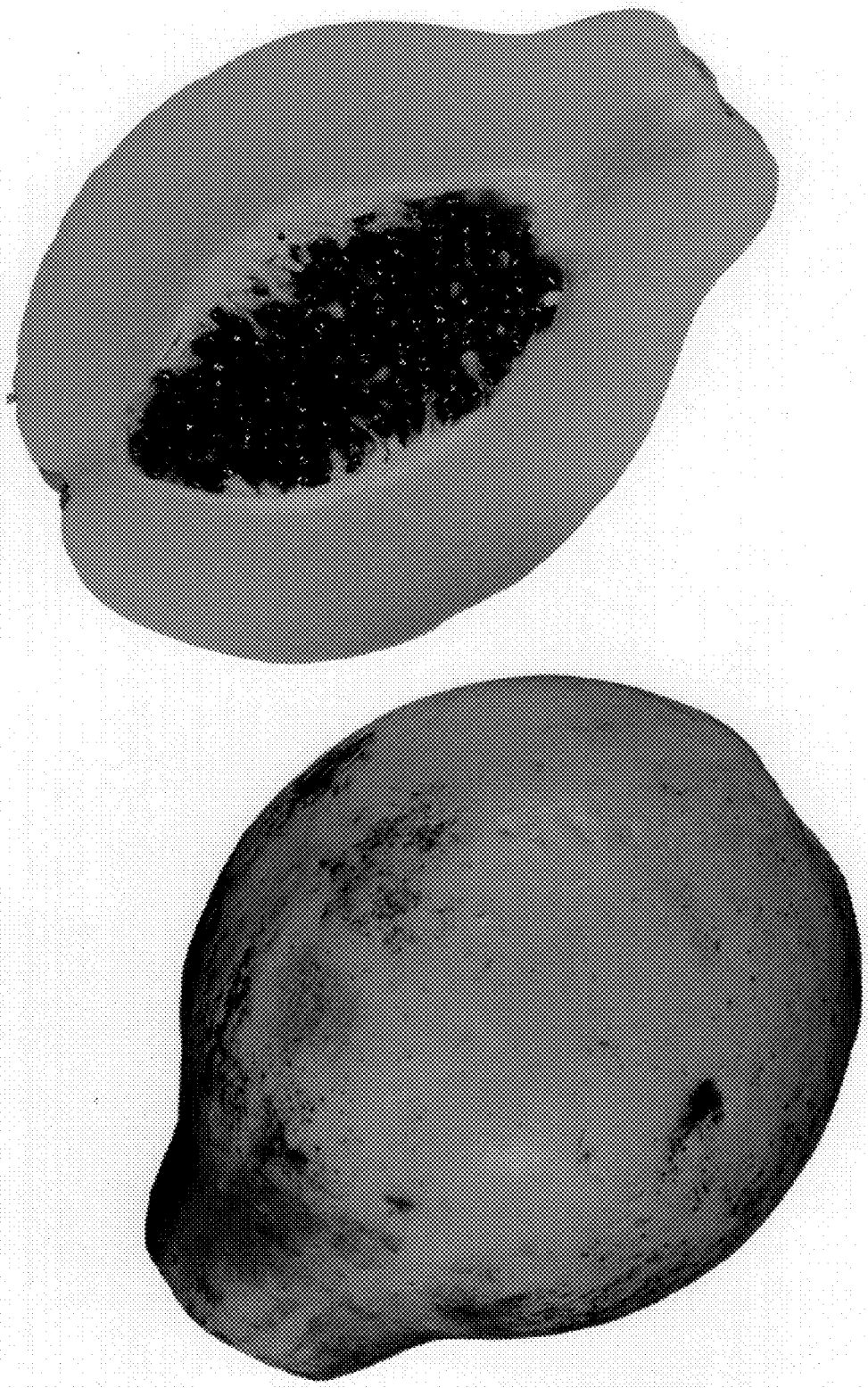
FIG. 3 shows fully ripe mature fruits, one has been sectioned to reveal the seed cavity form and flesh coloration, and the other is uncut to show typical ripe fruit skin color.

The new variety of papaya is most similar to the commercial papaya variety 'UH Rainbow' by having similar high tree vigor, deep orange-yellow flesh color, flesh thickness, total soluble solids, and PRSV-resistance. It is distinguished therefrom and an improvement thereon in a number of fruit and tree characteristics, such as increased fruit firmness, spicy flavor, attractive bulbous pyriform fruit shape, shiny, waxy skin surface, and somewhat smaller fruit size.

The new variety is similar to 'Kapoho' in sweetness. It is distinguished therefrom and an improvement thereon in having larger fruit size, PRSV-resistance, smooth, shiny, waxy skin surface generally free of deep grooves and lumps, deeper flesh color, spicy rather than strong odor, earlier and lower bearing height, and increased tree vigor. 'Poamoho Gold' lacks the strong odor associated with 'Kapoho' which some consumers find unpleasant. Instead its milder but distinct flavor described as 'spicy' makes it desirable. Ten months after planting, 'Poamoho Gold' trees are a little shorter but larger in diameter compared to 'Kapoho' in the Poamoho experiment. Height of first bud/fruits of 'Poamoho Gold' is slightly lower than 'Kapoho'.

The following is a detailed description of the new and distinct variety of papaya plant grown in the environments of Poamoho, Helemano, Kunia, Keaau, and Kapoho, Hi. on the islands of Oahu and Hawaii and is believed to apply to plants of the variety grown under similar condtions of soil and climate elsewhere. Where numeric values presented in the Detailed Description are followed by a "±" they represent the arithmetic mean plus or minus one standard error. In the following description, color references are made to The Royal Horticultural Society Colour Chart except where general terms of ordinary significance are used. Age is as given.

PLANT

Plant type: Arboreal monopodial.
Adaptation: Tropical lowland.
Maturity: 350 days from seeding to first harvest; 150 days from pollination to first harvest.
Size: Large, at 9 months after planting in Poamoho, Hi., 247.7±4.4 cm tall, 13.3±0.3 cm diameter.
Height at first harvest: 9 months after planting in Poamoho, Hi.: 247.7±4.4 cm.
Trunk diameter at first harvest, measured at 8 cm above the soil level at 9 months after planting in Poamoho, Hi.: 13.3±0.3 cm.
Plant gender: Gynodioecious, hermaphrodite trees.
Bark surface: Smooth.
Vigor: Vigorous.
Foliage density: 20–40 leaves at the apex.
Production: 5.3±0.6 fruits/tree/week, for 52 weeks.
Bearer: Fruit productivity varies between years, sites, and crop age.
Bark texture: Smooth with protruding nodal scars.
Bark color: Yellow-white group 159A.
Branches: (Evaluation from 1 cm diameter branches).
Branch texture: Smooth with protruding nodes.
Few branches form during the first year of growth: Older trees develop 1–5 branches thereafter.
Shoot color of current season's growth from shoots ranging from 1–2 cm in diameter: Yellow-white group 159A.

LEAVES

Measurements were taken from fully mature leaves of current season growth.

Size:
*Leaf lamina length* 8 *months after planting in Poamoho, Hi.*—71.4±1.8 cm.
*Leaf lamina width* 8 *months after planting in Poamoho, Hi.*—69.3±1.4 cm.
Form: Shallowly lobed palmate.
Number of lobes per leaf, 10-month-old tree: 9.
Apex: Acuminate.
Base: Cordate.
Texture, adaxial surface: Smooth.
Texture, abaxial surface: Moderately textured due to the raised veins having net-like or reticulated patterns.
Margin: Smooth shallowly lobed, slightly wavy.
Color: Upper surface glabrous: Green group 137A. Lower surface: Green group 137C.
Leaf venation pattern of the adaxial leaf surface: Each of the 9 lobes contains a major vein with alternating minor veins radiating from the major vein.
Leaf vein color, adaxial surface: Ranges from red group 51C to greyed-white group 156B.
Leaf venation pattern of the abaxial leaf surface: Each of the 9 lobes contains a major vein with alternating minor veins radiating from the major vein. The veins viewed from the adaxial are smooth but are raised in a textured pattern on the abaxial surface and therefore appear more pronounced.
Leaf vein color, abaxial surface: Yellow-green group 144B.
Petiole: Yellow-green group 144C near lamina for most of the petiole surface as an undercolor with medium purple coloration (greyed-purple group 186C) as an overcolor generally extending over the leaf midrib as well as the major secondary veins of the leaves.
Petiole length, 20 months after planting in Kapoho, Hi.: 104.7±2.5 cm.
Petiole diameter, 20 months after planting in Kapoho, Hi.: 173±0.02 cm.

FLOWERS

Flower buds, staminate:
*Size.*—3.8±0.04 cm long, 1–2 days pre-anthesis.
*Form.*—Bud consists of 5 coalescent petals that form a salverform corolla tube.
*Diameter of corolla tube* 1 *cm above the base,* 1–2 *days pre-anthesis.*—4.6±0.4 mm.
*Diameter of unopened free petals,* 1–2 *days pre-anthesis.*—0.9±0.2 cm.
Flower buds, hermaphrodite:
*Size.*—4.0±0.05 cm long, 1–2 days pre-anthesis.
*Form.*—Bud consists of 5 coalescent petals that form a swollen salverform corolla tube due to the presence of a functional ovary.
*Diameter of corolla tube at the widest part,* 1–2 *days pre-anthesis.*—1.1±0.3 cm.
*Diameter of the hermaphrodite bud, unopened free petals.*—1.0±0.2 cm.

Bud color, staminate and hermaphrodite: Yellow group 4D, 1–2 days pre-anthesis.

Flowers:

*Blooming period.*—Abundant year-round.

*Typical and observed flower types.*—Hermaphrodite papaya trees produce 3 types of flowers, staminate with functional anthers and abortive ovaries, perfect flowers with functional anthers and ovaries, and, occasionally, carpellodic flowers that resemble pistillate flowers with a 5-carpelled ovary and a variable number of stamens up to five that sometimes fuse with the carpel and result in misshapen fruit.

*Flower size.*—5.2±0.5 cm long, staminate or hermaphrodite.

*Flower fragrance.*—A combination of ginger and jasmine.

*Flower number per node.*—One, two, or three types of flowers are borne at each node depending on the age of the tree, season, and water and nutritional status of the plant. Flowers are either solitary or clustered. When clustered, the inflorescence is a cyme consisting of 2–9 buds, but 2–4 is typical.

*Diameter of cyme including buds and flowers.*—9.3±0.08 cm.

Petals, staminate:

*Petal shape.*—Non-coalescent part: Simple oblong.

*Petal length.*—Non-coalescent part: 2.2±0.5 cm, typically 5.

*Petal width.*—0.79±0.1 cm at the widest part.

*Petal apex.*—Rounded.

*Petal base.*—Narrower than widest part of width, 0.3±0.1 cm.

*Corolla base diameter.*—0.5±0.1 cm.

Petals, hermaphrodite:

*Petal shape.*—Non-coalescent part: Simple oblong.

*Petal length.*—Non-coalescent part: 2.5±0.3 cm, typically 5, fewer and shorter if the hermaphrodite flowers are carpellodic and misshapen.

*Petal width.*—1.0±0.1 cm at the widest part.

*Petal apex.*—Rounded.

*Petal base.*—Narrower than widest part of width, 0.5±0.05 cm.

*Corolla base diameter.*—0.8±0.06 cm.

*Petal margin, staminate and hermaphrodite.*—Simple, smooth.

*Petal texture, staminate and hermaphrodite.*—Smooth inner surface, smooth and waxy outer surface.

*Petal color, staminate and hermaphrodite, inner surface.*—Yellow group 11D.

*Petal color, staminate and hermaphrodite, outer surface.*—Yellow group 4D.

Sepals, staminate flowers:

*Sepal shape.*—Simple, wide at base, rounded at apex.

*Sepal number.*—5 with bases coalesced.

*Sepal length.*—2.3±0.4 mm.

*Sepal width at base.*—1.5±0.2 mm.

*Sepal apex.*—Acute.

*Sepal margin.*—Smooth.

*Sepal color, inner surface.*—Yellow-green group 145A.

*Sepal color, outer surface.*—Yellow-green group 145A.

Sepals, hermaphrodite flowers:

*Sepal shape.*—Simple, wide at base, rounded at apex.

*Sepal number.*—5 with bases coalesced.

*Sepal length.*—2.3±0.4 mm.

*Sepal width at base.*—3.6±0.2 mm.

*Sepal apex.*—Acute.

*Sepal margin.*—Smooth.

*Sepal color, inner surface.*—Yellow-green group 145A.

*Sepal color, outer surface.*—Yellow-green group 145A.

Stamens, staminate and hermaphrodite flowers:

*Stamen quantity.*—10.

*Stamen size, 1–2 days pre-anthesis.*—4.0–4.2 mm long, 0.7 mm diameter.

*Stamen filament color.*—Yellow-white group 158D.

*Anther quantity.*—10 with double sacs.

*Anther size.*—2.2±0.1 mm long.

*Anther color.*—Yellow-orange color group 20B.

*Pollen.*—Present in hermaphrodite and staminate flowers.

*Pollen color.*—Evaluated after screening and drying, within a glass vial: Yellow-white group 158C.

*Pollen quantity.*—Copious.

*Pollen size.*—Small.

Stigma, staminate flowers, 1–2 days pre-anthesis:

*Stigma quantity, staminate flower.*—1, undeveloped, no lobes.

*Stigma size.*—<0.1 mm in diameter and 0.1 mm long.

*Stigma color.*—Yellow-green group 154B.

*Style quantity.*—1.

*Style length.*—0.9±0.1 cm.

*Style color.*—Yellow-white group 158D.

*Ovary quantity, staminate flower.*—1, underdeveloped.

*Ovary size.*—1.3±0.04 mm diameter, 1.4±0.02 mm long.

*Ovary color.*—Yellow-green group 149C.

*Stigma, hermaphrodite flowers, 1–2 days pre-anthesis.*—1 with 5 lobes subdivided into 4–9 sections.

*Stigma size.*—9.2±0.5 mm in diameter and 4.1±0.4 mm long.

*Stigma color.*—Yellow-green group 154B.

*Style quantity.*—1.

*Style length.*—1.3±0.1 mm.

*Style color.*—Yellow-white group 158D.

*Ovary quantity, hermaphrodite flower.*—1.

*Ovary size.*—1.1±0.2 cm diameter, 1.4±0.2 cm. long.

*Ovary color.*—Yellow-green group 149C.

*Self-fertility.*—Hermaphrodite plants are self-fertile.

FRUIT

Maturity: 350 days from seeding to first harvest; 150 days from pollination to first harvest.

Date of first picking: Jan. 8, 1998.

Date of last picking: Dec. 21, 1999.

Size: The average fruit mass of 32 fruits in Poamoho from 1/99–7/99 was 541±12 g/fruit. Fruit mass at harvest can be manipulated by the degree of fruit thinning. For 'Kapoho' in the same field test, the average fruit mass from 167 fruits was 365±38 g/fruit.

Form: Pyriform to globular.

Average number per peduncle: Single or double.

Shape: Pyriform with neck absent or short neck.

Surface: Smooth.

Fruit abscission: When overripe.

Base attached to peduncle: Generally flattened with 5-point star pattern on hermaphrodites.

Fruit apex shape: Rounded with a slight depression for the pistil point.

Pistil point: Slightly depressed.

Typical and observed fruit length: From 10-month-old plants: 10.9±0.5 cm.

Typical and observed fruit diameter: From 10-month-old plants: 7.6±0.3 cm.
Typical and observed seed cavity length: From 10-month-old plants: 7.8±0.4 cm.
Typical and observed seed cavity width: From 10-month-old plants: 3.5±1.5 cm.
Seed cavity: Cross-sectional Shape: five-to eight-armed star.
Cavity:
*Length.*—7.57±0.31 cm for 597±65 g fruit from 20-month-old trees in Keaau, Hi.
*Width.*—3.56±0.16 cm for 597±65 g fruit from 20-month-old trees in Keaau, Hi.
*Stem.*—The peduncle is of average thickness (1.25±0.07 cm) and length (6.35±0.34 cm).
*Stem (peduncle) color.*—Greyed-orange group 164C.
Skin:
*Astringency.*—Slight amount noted.
*Thickness.*—Thin, less than 1 mm thick.
*Texture.*—Average, medium-firm to firm.
*Tenacity.*—Tenacious to flesh.
*Tendency to crack.*—Low.
*Pubescence.*—None.
*Color.*—Yellow-orange group 21A.
*Overcolor.*—Freckles and spots occasionally present depending on the season especially with lapses in fungicide application. Some may be physiological, others may be pathogen-induced hypersensitivity responses.
*Mottling color.*—Yellow-green group 152C.
*Freckles.*—Present. Color is greyed-orange group 165B.
Flesh:
*Color.*—Yellow-orange group 23B.
*Juice.*—Yellow-orange group 21D.
*Texture.*—Smooth to slightly grainy.
*Fibers.*—None except for vasculature that can be coarse.
*Ripens.*—Evenly over most of the fruit, but the stem end ripens last.
*Flavor.*—A tasteful balance between sugars, acids, and aromatics.
*Eating quality.*—Exceptionally high.
*Brix.*—13.2±0.58° Brix, the average from 32 'Poamoho Gold' fruits from monthly harvests from 1/99–7/99; 13.7±0.38° Brix, the average from 167 'Kapoho' fruits from the same field and the same time interval.
*Acidity.*—Medium.
*Aroma.*—Ranges from mildly ginger-like that is enhanced by higher sweetness to very ginger-like and spicy.
*Bitterness.*—Not bitter.

SEEDS

Measurements were made from seeds taken from fruit having an average fruit mass of 600 g.

Attachment: To parietal placenta.
Typical and observed number of seeds per fruit: 750.
Size:
*Average mass.*—15.8±0.06 mg.
*Average diameter.*—4.2 mm±0.07 mm.
*Average length.*—5.4 mm±0.12 mm.
*Apex.*—Gently pointed at an apical tip. Tip is prominent but not sharp.
*Base.*—Gently rounded, slightly flattened.
*Surface.*—Highly textured with parallel ridges (wings) along the longitudinal axis.
*Ridges.*—Corky.
*Tendency to split.*—None.
*Color.*—Brown group 200A.
*Kernel.*—Form generally well-filled teardrop shape.
*Taste.*—Astringent.
*Viability.*—Viable for over 1 year when stored at 4° C.
*Winter hardiness of cultivar.*—Winter in Hawaii typically is about 5–10 degrees cooler than summer. The 'Poamoho Gold' cultivar continues to grow and produce fruit in winter at elevations up to about 150 m above sea level, although at a lower frequency and sweetness. At elevations over 300 m, the trees cease fruit production. At temperate zone elevations of 1000–1500 m, the trees will freeze.

DISEASE AND INSECT RESISTANCE

Papaya mosaic virus: Untested.
Papaya leaf distortion mosaic virus: Untested.
Papaya ringspot virus: Resistant.
Powdery mildew: Susceptible.
Phytophthora root rot: Somewhat tolerant.
Use: Fresh market papaya for use in local markets as well as for long distance shipping.
Keeping quality: Good.

The present new variety of papaya tree, its flowers, foliage, and fruit herein described may vary in slight detail due to climatic and soil conditions, and cultural practices under which the variety may be grown; the present description is that of the variety grown under the ecological conditions prevailing in Central and Northwestern Oahu (Poamoho, Kunia, and Helemano) and Eastern Hawaii (Keaau and Kapoho).

What is claimed is:

1. A new and distinct variety of papaya plant, substantially as illustrated and described herein.

* * * * *